United States Patent [19]

Sone et al.

[11] Patent Number: 4,895,802

[45] Date of Patent: Jan. 23, 1990

[54] DNA STRAND CODING FOR α-ACETOLACTATE DECARBOXYLASE AND YEAST TRANSFORMED WITH THE DNA STRAND

[75] Inventors: Hidetaka Sone; Junichi Tanaka; Takashi Inoue, all of Takasaki, Japan

[73] Assignee: Kirin Beer Kabushiki Kaisha, Shibuya, Japan

[21] Appl. No.: 940,596

[22] Filed: Dec. 11, 1986

[30] Foreign Application Priority Data

Dec. 13, 1985 [JP] Japan .................................. 60-280289

[51] Int. Cl.$^4$ ....................... C12N 15/00; C12N 7/00; C07H 13/12
[52] U.S. Cl. ................................ 435/172.3; 435/232; 435/320; 435/940; 536/27; 426/11; 426/20
[58] Field of Search ....................... 435/172.3, 232, 320, 435/317.1, 940; 935/56, 69; 426/11, 20; 536/27

[56] References Cited

U.S. PATENT DOCUMENTS 4,617,273 10/1986 Olsen .................................... 435/232

FOREIGN PATENT DOCUMENTS 0128714 12/1984 European Pat. Off. ......... 435/172.3
0163491 4/1985 European Pat. Off. ............. 435/232

OTHER PUBLICATIONS

Carlsberg Res. Commun., vol. 48, 1983, pp. 239–247; S. E. Godtfredsen "On the Occurrence . . . Microorganism" *Whole Article*.
EBC Congress 1983, vol. 89, Lecture No. 17, pp. 161–168; S. E. Godtfresen et al.: "Use of . . . of Beer" * Whole Article*.
Journal of Biotechnology, vol. 5, 1987, pp. 87–91, Elsevier Science Pub. B.V. (Biomedical Division): Sone et al.: "Molecular . . . Aerogenes".
Acetolactate Decarboxylase from Aerobacter Aerogenes Eur. J. Biochem 14:133 (1970) Loken & Stormer.
2, 3 Butanediol Biosynthetic System . . . Stormer & Wood, Methods in Enz. 41:518 (1975).
Use of Acetolactate . . . Proc. Eur. Brewery Convention 1983, p. 161, Godtfredson.

*Primary Examiner*—Robin Teskin
*Attorney, Agent, or Firm*—Ladas & Parry

[57] ABSTRACT

DNA strand having an ability in biotechnological production of α-acetolactate decarboxylase is disclosed. The DNA strand is characterized in that it has a nucleotide sequence coding for a polypeptide whose amino acid sequence is substantially from A to B of FIG. 1 and which has α-acetolactate decarboxylase activity. Also disclosed is a yeast which belongs to *Saccharomyces cerevisiae* and which has been transformed by the DNA strand. The yeast is characterized by the face that its α-acetolactate producing ability is reduced, and will thus produce an alcoholic liquor such as beer which contains no or little diacetyls which have come from their precursor, namely α-acetolactate.

14 Claims, 3 Drawing Sheets

FIG. 1

AAGCTTGCATCCAGTTCCCCCTCCGCCAGCATCGCCGTCAGAGAAGACATATTGGCCTC

CACCTGGTGTACCTGCACCGCCATGTTCTGTACCTGAAACTGACGAATGAGCGCGAAAAT

TTTGGGATGAAAAGCATCTGAACTGGTGATGCCAATCGACAGGTTGCCGTTCAGACCGCG

CGCGATGCCGCGGGCTTTCTCCAGCGCGGCGTCGCTCAGCGCCAGGATCTTACAGGCGTC

CTCGTAGAAGGCTTCTCCCGCTTCGGTTAGCTCCACACCTCTCGTCAGACGCCTGAACAG

CGGCGTGCCCACTTCCTCTTCGAGCCGTTTGATCTGCTGACTCAGAGGAGGCTGTGAAAT

ACCCAGCGCTTTGGCCGCCCTGGTGAAGTGTCGCTCGCGTGCAACCGCGACAAAATACCG

CAGATAACGAAGTTCCATATCAAAAACGTCTCAAACCAGCATGGATTCTATATTGGAACT

CTCTGCTGAATCGGGTCAACATTTATTTAACCTTTATAAATAAAGTTGAAGAGGACGAGC

A
      10       20       30       40       50       60
↓ ATGATGATGCACTCATCTGCCTGCGACTGTGAGGCGAGCTTATGCGAGACCCTGCGCGGG
   MetMetMetHisSerSerAlaCysAspCysGluAlaSerLeuCysGluThrLeuArgGly       70       80       90      100     110     120
TTCTCCGCTAAACATCCTGACAGCGTGATCTATCAGACATCGCTAATGAGCGCCCTGCTA
PheSerAlaLysHisProAspSerValIleTyrGlnThrSerLeuMetSerAlaLeuLeu     130     140     150     160     170     180
AGCGGTGTCTACGAAGGGGACACCACCATCGCCGATCTGCTGGCACATGGTGATTTTGGT
SerGlyValTyrGluGlyAspThrThrIleAlaAspLeuLeuAlaHisGlyAspPheGly     190     200     210     220     230     240
CTGGGCACCTTCAACGAGCTGGACGGCGAAATGATTGCCTTCAGCAGCCAGGTGTACCAG
LeuGlyThrPheAsnGluLeuAspGlyGluMetIleAlaPheSerSerGlnValTyrGln     250     260     270     280     290     300
CTGCGCGCCGACGGCAGCGCACGCGCCGCGAAGCCAGAGCAGAAAACGCCGTTCGCGGTG
LeuArgAlaAspGlySerAlaArgAlaAlaLysProGluGlnLysThrProPheAlaVal     310     320     330     340     350     360
ATGACCTGGTTCCAGCCGCAGTACCGCAAAACCTTTGATGCGCCGGTCAGCCGTCAGCAG
MetThrTrpPheGlnProGlnTyrArgLysThrPheAspAlaProValSerArgGlnGln     370     380     390     400     410     420
ATCCACGACGTGATCGACCAGCAAATTCCCTCGGATAACCTGTTCTGCGCGCTGCGCATC
IleHisAspValIleAspGlnGlnIleProSerAspAsnLeuPheCysAlaLeuArgIle     430     440     450     460     470     480
GACGGCAACTTCCGCCACGCCCACACCCGTACCGTACCGCGTCAGACGCCGCCATACCGC
AspGlyAsnPheArgHisAlaHisThrArgThrValProArgGlnThrProProTyrArg     490     500     510     520     530     540
GCGATGACCGACGTGCTGGACGACCAGCCGGTGTTCCGCTTTAACCAGCGTGAAGGGGTG
AlaMetThrAspValLeuAspAspGlnProValPheArgPheAsnGlnArgGluGlyVal     550     560     570     580     590     600
CTGGTTGGGTTCCGCACGCCGCAGCATATGCAGGGCATCAACGTGGCCGGCTATCACGAA
LeuValGlyPheArgThrProGlnHisMetGlnGlyIleAsnValAlaGlyTyrHisGlu     610     620     630     640     650     660
CATTTCATTACCGACGACCGTCAGGGCGGGGGACATCTGCTGGATTACCAGCTGGAGAGC
HisPheIleThrAspAspArgGlnGlyGlyGlyHisLeuLeuAspTyrGlnLeuGluSer     670     680     690     700     710     720
GGCGTGCTCACCTTTGGCGAAATACACAAGCTAATGATTGACCTGCCCGCCGACAGCGCG
GlyValLeuThrPheGlyGluIleHisLysLeuMetIleAspLeuProAlaAspSerAla  B     730     740     750     760     770     780 ↑
TTTTTACAGGCCAACCTTCACCCCAGCAACCTTGATGCAGCGATCCGTTCCGTCGAAAAC
PheLeuGlnAlaAsnLeuHisProSerAsnLeuAspAlaAlaIleArgSerValGluAsn

TAACAGGAGAACTATCGTGAACAGTGAGAAACAGTCACGTCAGTGGGCGCACGGCGCCGA
***

TATGGTTGTCGGCCAGCTGGAAGCGCAGGGCGTGAAGCAGGTGTTCGGGATC

DNA STRAND CODING FOR α-ACETOLACTATE DECARBOXYLASE AND YEAST TRANSFORMED WITH THE DNA STRAND

BACKGROUND OF THE INVENTION

1. Field of the Art

This invention relates to a DNA strand having an ability in biotechnological production of α-acetolactate decarboxylase (hereinafter called α-ALDCase) as produced by *Enterobacter aerogenes* IFO 13534 and to a yeast belonging to *Saccharomyces cerevisiae* transformed with the DNA strand so that its α-acetolactate (hereinafter called α-AL) producing ability is reduced.

2. Prior Art

Alcoholic beverages such as beer, sake, wine, etc., are generally produced by adding a yeast belonging to *Saccharomyces cerevisiae* to a starting material liquid for fermentation such as wort, fruit juice, etc., and subjecting the mixture to alcohol fermentation. In the fermentation process, the yeast will produce α-AL as the intermediate substance for biosynthesis of valine and leucine which are amino acids necessary for the growth of itself, and leak it inevitably out of the cell, namely into the fermented liquor. The α-AL which has thus become to exist in the fermented liquor will change spontaneously to diacetyl (hereinafter called DA) through the non-enzymatical reaction in the fermented liquor.

DA is a substance having strong objectionable odor called generally as "cooked odor" or "DA odor" and, in order to produce an alcoholic beverage excellent in flavor (namely without DA odor), the content of α-AL and DA in the fermented liquor is required to be decreased to a low level so that the total DA content will not finally exceed the discrimination threshold of DA odor in the alcoholic beverage (e.g. 0.05 to 0.1 mg/liter in the case of beer) even if α-AL may be all changed to DA.

While DA in the fermented liquor is converted to acetoin which is tasteless and odorless relatively rapidly in the co-presence of yeast, α-AL in the fermented liquor will not be changed by yeast, but it becomes decomposable with yeast only after it is changed to DA by non-enzymatical chemical reaction. However, since the reaction from α-AL to DA in the fermented liquor proceeds at a very slow rate, this reaction becomes the rate-limiting step, whereby the fermented liquor is required to be aged under the co-presence of yeast for a long time in order to obtain an alcoholic liquor with low content of α-AL and DA (namely without DA odor).

α-ALDCase is an enzyme having the property of converting α-AL to acetoin and has been known to be produced by various kinds of bacteria such as *Enterobacter aerogenes, Bacillus licheniformis, Lactobacillus casei, Bacillus brevis, Enterobacter cloacae, Acetobacter* bacteria (such as *A. rancens, A. aceti*, etc), etc. The principal enzymological properties of the α-ALDCase produced by *Enterobacter aerogenes* were investigated by the present inventors to obtain the results shown below.

Molecular weight: 28000~29000
Isoelectric point: pH 5.0~6.0
Optimal pH: 6.5~7.5
Optimal temperature: 40°~50° C.
Thermal stability: stable to around 60° C.

There is also a report about the enzymological properties of the α-ALDCase produced by *Enterobacter aerogenes* [European Journal of Biochemistry (Eur. J. Biochem.) 14 (1970) 133–137]

SUMMARY OF THE INVENTION

The present invention provides a DNA strand having an ability in biotechnological production of α-ALDCase, which is useful for production of alcoholic beverages having no DA odor within by far shorter period as compared with the prior art method, and a yeast of which α-AL producing ability is reduced by transformation with the DNA strand.

More specifically, the DNA strand having an ability in biotechnological production of α-ALDCase according to the present invention is characterized in that it has a nucleotide sequence, or, in other words, a base sequence coding for a polypeptide having α-ALDCase activity, of which amino acid sequence, namely an amino acid sequence of the polypeptide, is substantially from A to B of the amino acid sequence shown in FIG. 1.

On the other hand, the yeast belonging to *Saccharomyces cerevisiae* according to the present invention is characterized in that its α-AL producing ability is reduced by transformation with a DNA strand which has a nucleotide sequence coding for the polypeptide having α-ALDCase activity, of which amino acid sequences is substantially from A to B of the amino acid sequence shown in FIG. 1.

The present invention also relates to the use of the DNA strand and the yeast.

The DNA strand according to the present invention can impart α-ALDCase producing ability to various microorganisms, for example, *Saccharomyces cerevisiae* to reduce its α-AL producing ability (as described in detail below), or it can be effectively utilized in biotechnological production of α-ALDCase.

Also, since the yeast according to the present invention is reduced in its ability to produce α-AL (correctly leaking of α-AL out of the cell), if the starting material liquor for fermentation is fermented with this yeast, the level of α-AL in the fermented liquor will become very low to give a result that the aging period required for treatment of α-AL in the fermented liquor, and therefore the production period of alcoholic beverage can be remarkably shortened. In the yeast of the present invention, its α-AL producing ability is reduced probably because the α-AL, even if produced within the cell in the fermentation process, will be converted to acetoin by α-ALDCase also produced within the cell.

BRIEF DESCRIPTION OF THE DRAWINGS

FIG. 1 illustrates the nucleotide sequence of the DNA strand according to the present invention and the amino acid sequence deduced from the nucleotide sequence;

DETAILED DESCRIPTION OF THE INVENTION

α-ALDCase gene

Definition

The DNA strand according to the present invention having an ability in biotechnological production of α-ALDCase, namely the α-ALDCase gene, codes for a polypeptide having α-ALDCase activity, of which amino acid sequence is substantially from A to B of the amino acid sequence shown in FIG. 1.

Here, the "DNA strand" means complementary double strands of polydeoxyribonucleic acid having a certain length. And, since the "DNA strand" is specified by the amino acid sequence of the polypeptide encoded thereby and the polypeptide has a finite length as mentioned above, the DNA strand also has a finite length. However, while the DNA strand contains a gene coding for α-ALDCase and is useful for biotechnological production of the polypeptide, such biotechnological production cannot be effected only by the DNA strand having the finite length, but biotechnological production of the polypeptide is rendered possible under the state where a DNA strand of a suitable length is linked upstream to its 5'-side and/or downstream to its 3'-side.

Accordingly, the "DNA strand" as mentioned in the present invention is inclusive, in addition to the DNA strand of a specific length (the length of A–B in terms of the corresponding amino acid sequence in FIG. 1), of those in the form of a linear DNA or a circular DNA strand containing the DNA strand of the specific length.

Of the existing forms of the DNA strand according to the present invention, typical are the plasmid form containing the DNA strand as a part of the constituent and the form existing in a microorganism, particularly E. coli and yeast, as the plasmid form or the integrated form into the genome.

The preferable existing form of the DNA strand according to the present invention comprises the DNA strand of the present invention as a foreign gene linked to a promoter and a terminator so that the α-ALDCase gene can be expressed stably in a microorganism, which exists in the microorganism as a plasmid form or and integrated form into the genome. As the promoter and the terminator, known promoters and terminators can be used in a suitable combination.

Polypeptide Encoded by the Gene

As mentioned above, the DNA strand according to the present invention is specified by the amino acid sequence of the polypeptide encoded thereby. The polypeptide has α-ALDCase activity and has an amino acid sequence which is substantially from A to B of the amino acid sequence shown in FIG. 1. Here, "amino acid sequence which is substantially from A to B of the amino acid sequence shown in FIG. 1" indicates that some of the amino acids can be deleted, substituted or added, etc., so long as the peptide has α-ALDCase activity.

A typical polypeptide having α-ALDCase activity in the present invention is from A to B of the amino acid sequence in FIG. 1, consisting of 260 amino acids, which amino acid sequence has not been known in the prior art.

Nucleotide Sequence of DNA Strand

The DNA strand coding for α-ALDCase includes one having the nucleotide sequence from A to B in FIG. 1 and those having nucleotide sequences corresponding to the changes in amino acid sequence of α-ALDCase as mentioned above, or degenerative isomers thereof. Here, the "degenerative isomer" means a DNA strand which is different only in degenerative codon and can code for the same polypeptide. For example, relative to the DNA strand having the nucleotide sequence of A to B in FIG. 1, the DNA strand having a codon corresponding to any one of the amino acids changed from, for example, the codon (AAC) corresponding to Asn at the carboxy terminal end to, for example, AAT which is in degenerative relationship therewith, is called a degenerative isomer in the present invention.

A preferable specific example of the DNA strand according to the present invention has at least one stop codon (e.g. TAA) in contact with the 3'-side end.

Further, upstream to the 5'-side and/or downstream to the 3'-side of the DNA strand of the present invention, a DNA strand with a certain length can be continuous as the non-translation region (the initial portion downstream of the 3'-side is ordinarily a stop codon such as TAA).

The nucleotide sequence of the DNA strand shown in FIG. 1 was determined for the gene coding for the α-ALDCase cloned from *Enterobacter aerogenes* IFO 13534 according to the Maxam-Gilbert method and the dideoxy method.

Obtention of DNA Strand

One means for obtaining the DNA strand having the nucleotide sequence coding for the amino acid sequence of the above α-ALDCase is to synthesize chemically at least a part of the DNA strand according to the method for synthesis of polynucleotide.

In view of the fact that the number of amino acids of α-ALDCase is at least 260, rather than the chemical synthetic method mentioned above, it would be preferable to obtain the DNA strand from the genomic library of *Enterobacter aerogenes* IFO 13534 according to the method conventionally used in the field of genetic engineering, for example, the hybridization method with the use of a suitable probe.

In this invention, the present inventors cloned the DNA strand of the present invention from the above genomic library by use of the shot gun method, because the nucleotide sequence coding for the α-ALDCase of *Enterobacter aerogenes* IFO 13534 and the amino acid sequence of α-ALDCase were not known (see Examples shown below about its details).

Yeast With Reduced Ability to Produce α-Acetolactate

The DNA strand of the present invention cloned as described above contains the genetic information for making α-ALDCase, and therefore this can be introduced into the yeast used generally as the yeast for fermentation of alcoholic liquors (*Saccharomyces cerevisiae*) to transform the yeast, whereby a yeast for fermentation with reduced α-AL producing ability can be obtained.

Yeast

The yeast to be transformed in the present invention may be a yeast belonging to *Saccharomyces cerevisiae* as described in "The Yeasts, a Taxonomic Study" third edition (Yarrow, D., ed. by N. J. W. Kreger-Van Rij. Elsevier Science Publishers B.V., Amsterdam (1984), p. 379) and its synonym or a mutant, but for the purpose of the present invention, a yeast for fermentation of alcoholic liquors belonging to *Saccharomyces cerevisiae*, specifically beer yeast, wine yeast, sake yeast, etc., are preferred. Specific examples may include wine yeast: ATCC 38637, ATCC 38638, beer yeast: ATCC 26292, ATCC 2704, ATCC 32634, sake yeast: ATCC 4134, ATCC 26421, etc.

To further comment on the properties of these yeasts for fermentation, as the result of selection and pure cultivation over long years for the properties suitable for fermentation, namely efficient fermentation of the starting material liquid for fermentation, production of alcoholic liquors with good flavor and stable genetic properties, etc., as the index, they have become polyploids which will undergo genetically cross-segregation with extreme difficulty and have lost spore forming ability substantially completely. For example, in the case of beer yeast practically used, while it is enhanced in the ability to assimilate maltose, maltotriose which are sugar components in the wort, it has lost its wild nature, for example, it is crystal violet sensitive, etc.

Transformation

It has been confirmed for the first time by the present inventors that transformation of a yeast with the DNA strand of the present invention resulted in reduction of its α-AL producing ability. However, the procedure or the method itself for preparation of the transformant can be one conventionally employed in the field of molecular biology, bioengineering or genetic engineering, and therefore the present invention may be practiced according to these conventional techniques except for those as described below.

For expression of the gene of the DNA strand of the present invention in a yeast, it is first required that the gene should be carried on the plasmid vector existing stably in the yeast. As the plasmid vector to be used in this operation, all of the various kinds known in the art such as YRp, YEp, YCp, YIp, etc., can be used. These plasmid vectors are not only known in literatures, but also they can be constructed with ease.

On the other hand, for the gene of the DNA strand of the present invention to be expressed in a yeast, the genetic information possessed by the gene is required to be transcribed and translated. For that purpose, as the unit for controlling transcription and translation, a promoter and a terminater may be linked upstream to the 5'-side and downstream to the 3'-side of the DNA strand of the present invention, respectively. As such promoter and terminator, various kinds such as ADH, GAPDH, PHO, GAL, PGK, ENO, TRP, HIP, etc., have been already known and any of these can be utilized also in the present invention. These are not only known in literatures, but also they can be prepared with ease.

As the marker for selecting the transformant to be obtained by the present invention, a resistant gene to G418, hygromycin B, a combination of methotrexate and sulfanylamide, tunicamycin, ethionine, compactin, copper ion, etc., can be employed.

For having the DNA strand of the present invention held more stably in a yeast, this can be also integrated into the genome of the yeast. In this case, for making easier integration of the DNA strand of the present invention carried on the plasmid vector into the genome, it is desirable to insert a DNA having high homology with the genome DNA into the plasmid vector, and examples of DNA for this purpose may include rRNA gene, HO gene, etc.

Figure 3:
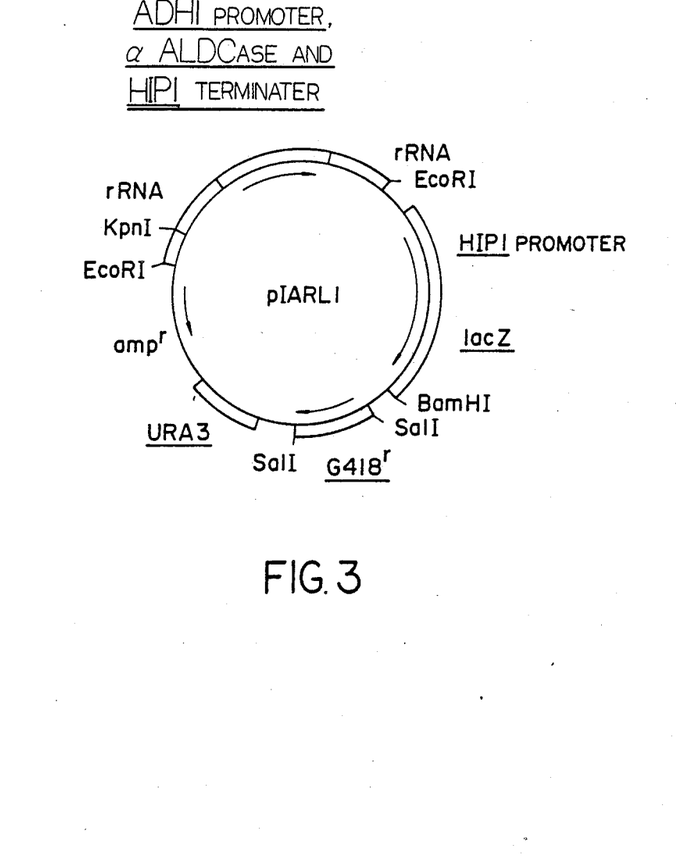
FIG. 3 illustrates the structure of pIARL1.

Among them, it has been known that rRNA gene is repeated tandemly for about 140 times in haploid yeast genome (Journal of Molecular Biology 40, 261–277 (1969)). Due to this specific feature, when this sequence is utilized as the target sequence for recombination there are the following advantages as compared with the case when utilizing other gene sequence. 1. It is expected that the transformation frequency may be elevated. 2. The change in the corresponding trait of the target sequence by recombination may be considered to be negligible. 3. By use of the plasmid having the structure as shown in Examples (pIARL1 in FIG. 3), it becomes possible to integrate a plural number of foreign genes into the genome by repeating a series of operations of integration of plasmid and excision of the vector sequence.

Also, the DNA strand which can be used for transformation of a yeast in the present invention can also code for a polypeptide different from the polypeptide of A to B shown in FIG. 1, so long as it has α-ALDCase activity, as mentioned previously. Examples of such polypeptide may include the polypeptide of A to B shown in FIG. 1 to which one or more of amino acids have been inserted or added, from which one or more amino acids have been deleted or substituted with other amino acids, and also α-ALDCase produced by *Bacillus licheniformis, Lactobacillus casei, Bacillus brevis, Enterobactor cloacae, Acetobacter* bacteria (*A. rancens, A. aceti*, etc. Such DNA strands would be readily available by utilizing contemporary genetic engineering techniques.

Transformation of a yeast with the plasmid thus prepared can be done according to any method suited for the purpose conventionally used in the field of genetic engineering or bioengineering, for example, the spheroplast method [Proceedings of National Academy of Sciences of the United States of America (Proc. Natl. Sci. USA), 75, 1929 (1978)], the lithium acetate method [Journal of Bacteriology (J. Bacteriol.), 153, 163 (1983)], etc.

The yeast of the present invention thus obtained is the same as the yeast before transformation in its geno type or phenotype except for the new trait according to the genetic information introduced by the DNA strand of the present invention (that is, endowed with α-ALDCase producing ability to consequently decompose α-AL within the cell, thereby lowering the amount of α-AL leaked out of the cell), the trait derived from the vector used and the defective corresponding trait due to the defect of a part of the genetic information during recombination of the gene which might have occurred. Further, the beer yeast obtained by integrating the DNA strand of the present invention into the yeast genome by use of YIp type plasmid, followed by excision of unnecessary vector sequence (see Example (6) shown below about its details) has no trait derived from the vector employed. Thus, the yeast of the present invention is substantially the same as the yeast for fermentation conventionally used. Accordingly, the yeast according to the present invention can be used under essentially the same fermentation conditions for the yeast for fermentation of the prior art, besides it has reduced α-AL producing ability in the fermented liquor, and therefore the α-AL content in the fermented liquor is consequently low, whereby the aging period of the fermented liquor required for its treatment can be remarkably shortened.

EXPERIMENTAL EXAMPLES (1) Cloning of α-ALDCase Gene (i) Purification of chromosomal DNA of α-ALDCase Producing Strain By culturing under aeration *Enterobacter aerogenes* IFO 13534 (procured from Institute for Fermentation, Osaka, Japan) in L-broth containing 0.5% glucose at 37°

C. for 10 hours, 0.5 g of wet microorganism cells was obtained.

This was resuspended in 5 ml of saline EDTA buffer [0.15M NaCl, 0.1M EDTA (pH 8.0)]. Subsequently, it was treated with 400 µg/ml of lysozyme (produced by Seikagaku Kogyo), 20 µg/ml of ribonuclease A (produced by Sigma Co.) at 37° C. for 20 minutes. Next, it was treated with 0.5% of sodium dodecylsulfate (SDS) and 500 µg/ml of proteinase K (produced by Sigma Co.) at 65° C. for 4 hours. This was loaded onto a previously prepared sucrose density gradient solution (50 mM tris-HCl (pH 7.4), 0.1M NaCl, 5 mM EDTA, 0.1% SDS, 5-20% sucrose), and subjected to centrifugation by Hitachi Ultra-centrifugal Rotor RPS 27 at 25 krpm at 20° C. for 3 hours. After fractionation in fractions each of 2.5 ml, the fractions were examined for molecular weight according to 0.4% agarose gel electrophoresis and the fractions containing high molecular weight DNA were collected. This was precipitated with ethanol and the precipitate was dissolved in 1 ml of TE buffer (10 mM tris-HCl (pH 8.0), 1 mM EDTA) and dialyzed against one liter of TE buffer. 300 µg of chromosomal DNA was obtained.

(ii) Preparation of Cosmid Library

120 µg of the chromosomal DNA obtained in (i) was partially digested with a restriction enzyme Sau3AI to about 40 kbp. This was loaded onto a previously prepared sucrose density gradient solution (20 mM tris-HCl (pH 8.0 ), 1M NaCl, 5 mM EDTA, 10-40% sucrose) and subjected to centrifugation by Hitachi Ultra-centrifugal Rotor RPS 27 at 26 krpm at 20° C. for 22 hours. After fractionation in fractions of each 0.5 ml, the fractions were examined for molecular weight by 0.4% agarose gel electrophoresis and the fractions containing DNA fragments of about 40 kbp were collected. After ethanol precipitation of the fractions, the precipitate was dissolved in 500 µl of TE buffer and dialyzed against one liter of TE buffer.

0.2 µg of the DNA fragments of about 40 kbp obtained was ligated with 0.3 µg of a cosmid pJB8 Arm (produced by Amersham International) by T4 ligase. This DNA was in vitro package by use of λ DNA in vitro packaging kit (produced by Amersham International) and was used to transfect E. coli DHI (F−, gyrA96, recA1, relA1, endA1, thi-1, hsdR17, supE44, λ−) [Journal of Molecular Biology (J. Mol. Biol.), 166 557-580 (1983): ATCC 33849] to obtain a cosmid library of E. aerogenes genome.

(iii) Screening of α-ALDCase Gene Holding Transductant

By selecting transductants exhibiting α-ALDCase activity from the cosmid library obtained in (ii), α-ALDCase gene holding transductants were obtained.

Specifically, 300 transductants from cosmid library were inoculated one by one onto L-agar medium containing 50 µg/ml of ampicillin and 0.5% of glucose, followed by cultivation at 37° C. for 8 hours, and each culture was assayed for α-ALDCase activity. That is, each transductant was suspended in 1 ml of 30 mM potassium phosphate buffer (pH 6.2) and vortexed vigorously with addition of 10 µl of toluene for 30 seconds. For the cell suspension, α-ALDCase activity was assayed following the method of Godfredsen et al. [Carlsberg. Research Communication (Carlsberg. Res. Commun., 47, 93 (1982)]. As the result, two α-ALDCase activity holding transductants were obtained. The plasmids of the clones obtained were designated as pCA3 and pCA13, respectively.

(iv) Determination of α-ALDCase Gene DNA Nucleotide Sequence

By carrying out subcloning from pCA13, the DNA fragment of 1.4 kbp excised with restriction enzymes BamHI and EcoRV was turned out to code for α-ALDCase. To the EcoRV site was ligated HindIII linker (dCAAGCTTG: produced by Takara Shuzo Co., Japan), and the ligated product was inserted between the cleavage sites of BamHI and HindIII of a plasmid pUC9 (produced by Pharmacia Co.) to construct a plasmid, which was designated as pUAR5.

For the BamHI-EcoRV fragment, DNA nucleotide sequence was determined according to the dideoxy method [Proc. Natl. Acad. Sci. USA, 74, 5463 (1977)] and the Maxam-Gilbert method [Proc. Natl. Acad. Sci. USA, 74, 560 (1977)] (FIG. 1). As the result of analysis of this nucleotide sequence, an open reading frame of 780 bp was found to exist. Here, it may be estimated that a protein having 260 amino acids and a molecular weight of 29000 is encoded, and the molecular weight was found to be substantially coincident with the above molecular weight of α-ALDCase.

(2) Introduction of α-ALDCase Gene into Yeast (i) Construction of ADH1 Promoter

From Saccharomyces cerevisiae S288C [α, suc2, mal, gal2, CUP1): Biochemical and Biophysical Research Communications (Biochem. Biophys. Res. Commun.), 50, 186-191 (1973): ATCC26108], chromosomal DNA was prepared according to a conventional method. According to the same method as described in Example (1) (ii), DNA fragments of about 10 kbp were obtained by partial digestion with the restriction enzyme Sau3AI. They were ligated with pBR322 cleaved with the restriction enzyme BamHI by T4 ligase to construct a genomic library. The synthetic oligomer corresponding to the nucleotide sequence from the seventh to the 36th in the coding region of ADH1 gene [Journal of Biological Chemistry (J. B. C.) 257, 3018 (1982)] was end-labelled with $^{32}P$ and by use of this as probe, ADH1 gene was cloned from the genomic library. Further, this was cleaved with restriction enzymes SphI and Sau3AI to obtain a DNA fragment of 542 bp containing the promoter and a part of the coding region of the ADH1 gene. By treating the Sau3AI end of this fragment with an endonuclease Bal31 to have the coding region completely lost, and thereafter HindIII linker (dCAAGCTTG: produced by Takara Shuzo Co., Japan) was ligated therewith. This DNA fragment was used as ADH1 promoter.

(ii) Construction of Expression Vector and Introduction into Yeast

By using basically the plasmid YEp13 (Gene, 8, 121 (1979): ATCC37115], an expression vector was constructed according to the following procedure.

First, SalI-SacI fragment and XhoI-SmaI fragment existing on both ends of the LEU2 gene of YEp13 were removed. By this, the plasmid became to have no cleavage site of the restriction enzymes XhoI, SacI, SmaI and BglII, but have only one cleavage site of the restriction enzyme SalI. Next, between the HindIII site derived from pBR322 and the HindIII site derived from 2 µm DNA in the plasmid, the synthetic oligonucleotide 41 mer was inserted. The synthetic oligonucleotide has the following nucleotide sequence containing the cleavage site of the restriction enzymes SacI, SmaI, BglII and XhoI:AGCTTATGATTACGAGCTCCCGG-GCAGATCTCGGCCTCGAGATACTAATGCT-CGAGGGCCCGTCTAGAGCCGGAGCTCTCGA. In the present invention, this plasmid was designated as YEp13K.

Next, the SphI-HindIII fragment of YEp13K was substituted with the ADH1 promoter prepared in (i) to construct an expression plasmid vector pAK503.

The plasmid pUAR5 having the α-ALDCase gene fragment obtained in (1) (iv) was cleaved with the restriction enzyme HincII and after addition of HindIII linker (dCAAGCTTG: produced by Takara Shuzo Co., Japan), cleaved with the restriction enzymes HindIII and BamHI. The HindIII-BglII fragment of pAK503 was replaced with the α-ALDCase gene fragment of 940 bp obtained to construct a plasmid pAL503.

Figure 2:
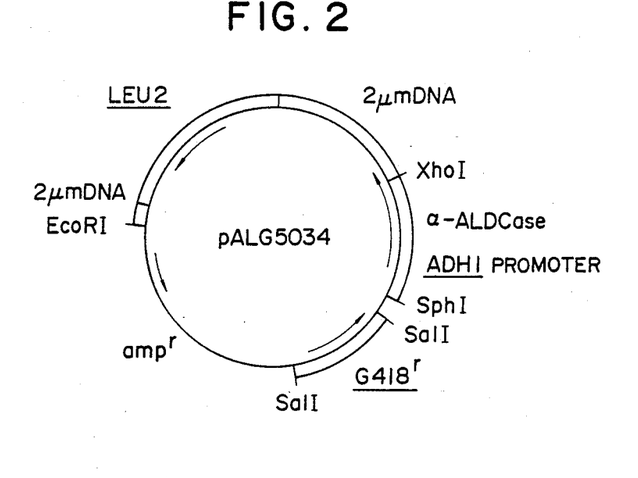
FIG. 2 illustrates the structure of pALG5034.

Further, pUC-4K (produced by Pharmacia Co.) containing the G418 resistant gene was cleaved with the restriction enzyme SalI, and the fragment containing the G418 resistant gene obtained was inserted at the SalI site of pAL503 to construct the desired plasmid pALG5034 (FIG. 2).

When pALG5034 was introduced into yeast [TD4 (a, his, ura, leu, trp; a mutant strain of Saccharomyces cerevisiae S288C) and beer yeast IFO 0751 strain] according to the lithium acetate method [Journal of Bacteriology (J. Bacteriol.) 153, 163, (1983)], α-ALDCase activities of 1.9-3.3 U/mg protein and 1.8-3.5 U/mg protein were exhibited, respectively.

The IFO 0751 transformed with pALG5034 is called SKB101 and the TD4 transformed with pALG5034 is called SKB102.

The α-ALDCase gene has three ATG's which is the translation initiation codon continuously at its 5'-end of the coding region. After removing one or two of the three ATG's from the 5'-side by treatment with endonuclease Bal31 from the HincII site of the 5'-side of the α-ALDCase gene fragment, the genetic information of the obtained fragments was expressed within the yeast TD4 to see the effect on the activity. As the result, no great difference in enzyme activity of the α-ALDCase obtained was recognized.

(3) Fermentation Test (Confirmation of Reduction in Amount of Diacetyl Produced)

Fermentation tests were conducted for the two kinds of yeasts of the TD4 and the IFO 0751 into which α-ALDCase gene had been introduced as described in (2)-(ii), and reduction of the amounts of the total diacetyl (hereinafter called TDA: TDA consists of vicinal diketones and acetohydroxy acids, mainly DA and its precursor α-AL) in the fermented wort by these transformed yeasts was confirmed according to the following method.

(i) Obtention of α-ALDCase Producing Yeast Cells

The two kinds of yeasts transformed with pALG5034 as described above (SKB101 and SKB102) and the respective host yeasts (IFO 0751 and TD4) were cultured in YPD medium. For the strains having introduced pALG5034, G418 was added into the medium to 600 μg/ml.

The respective cells grown by shaking cultivation at 30° C. for 16 hours were collected by centrifugation at 3000×g for 10 minutes, washed with distilled water and then provided for fermentation test.

(ii) Fermentation Test

To a wort prepared to 11° P was added the yeast obtained in (i) to a yeast addition ratio of 0.5% (wet. w/v) and, after sufficient aeration, stationary fermentation was carried out at 8° C. for 7 days. After completion of fermentation, the cells were removed by centrifugation at 3000×g for 10 minutes and filtration, and the filtrate was subjected to measurement of amount of TDA (total diacetyl amount).

The results were as shown in the following Table. In fermentation by use of the yeast of the present invention, it can be seen that TDA amount in the fermented wort is reduced to a great extent as compared with control strains.

The In Amount of Total Diacetyl (TDA) the Fermented Wort

| The in amount of total diacetyl (TDA) the fermented wort | |
|---|---|
| Strain | TDA (mg/liter) |
| TD4 ① | 0.26 |
| ② | 0.30 |
| Average | 0.28 |
| TD4 + pALG5034 ① | 0.03 |
| (SKB102) ② | 0.05 |
| Average | 0.04 |
| IFO0751 ① | 0.28 |
| ② | 0.28 |
| ③ | 0.32 |
| Average | 0.29 |
| IFO0751 + pALG5034 ① | <0.04 |
| (SKB101) ② | 0.07 |
| ③ | 0.07 |
| Average | <0.06 |

(4) Construction of Integration Type Plasmid (i) Structure and characteristic of Plasmid pIARL1

In order to have the α-ALDCase gene held stably within the yeast, a plasmid pIARL1 having no autonomously replicating ability which can be held by the yeast only through integration into the genome was constructed. The plasmid has the G428 resistant gene and the β-galactosidase gene as the markers within yeast and also has rRNA gene sequence as the sequence necessary for the plasmid to be integrated into the genome DNA by homologous recombination. The α-ALDCase gene is sandwiched between the ADH1 promoter at 5'-end and HIP1 terminater at 3'-end, and the combined fragment is inserted in the rRNA gene sequence. The plasmid, in order to be integrated efficiently into the rRNA gene on the chromosome, is cleaved previously at the KpnI site within the rRNA gene sequence before used for transformation. As the result, in the transformant obtained, the rRNA gene sequence derived from the plasmid exists next to that existing originally in the chromosome. Accordingly, when the transformant is grown in a complete medium, spontaneous recombination between the two rRNA gene sequences occurs, whereby G418 sensitive, Lac− cells will appear. A part of these will exhibit α-ALDCase activity, and only ADH1 promoter, α-ALDCase gene and HIP1 terminator remain on the chromosome in these cells, with other vector portions being excised.

(ii) Construction of pIARL1

The pIARL1 (FIG. 3) was constructed from a yeast integrating plasmid YIp5 (ATCC 37061, Gene, 8, 17-124 (1979), and Proc. Natl, Acad. Sci. USA 76, 1035-1039 (1979)).

(ii-1) Construction of pIRL9

First, the G418 resistant gene fragment prepared after cleavage of pUC4K (produced by Pharmacia) with SalI was inserted at the SalI site of YIp5 to construct a plasmid pIG7.

HIP1 promoter+lacZ gene fragment were then obtained as follows. First, plasmid pHIP1 having HIP1 gene was obtained from the genomic library of *S. cerevisiae* S 288C (ATCC 26108) referred to hereinabove through the use, as a probe, of a synthesized oligomer corresponding to the sequence of #46 to #75 bases in the coding region of HIP1 gene (Gene, 38, 205-214 (1985)) and having been labelled at its 5'-terminus. From the pHIP1 thus produced was obtained BglII fragment (HIP1 promoter) having ca. 0.6 kb of the 5'-non translation region and ca. 0.4 kb of the translation region. The BglII region thus produced was then ligated with lacZ gene obtained from plasmid pMC1871 (Pharmacia) as a BamHI fragment. The BglII-BamHI fragment (viz. HIP 1 promoter+lacZ gene fragment) thus obtained was then inserted into the BamHI site of pIG7 to construct plasmid pILG2.

Plasmid pRRN rRNA gene was cloned from the library used for cloning of the ADH1 gene (the genomic library of *S. cerevisiae* S288C (ATCC 26108)) referred to hereinabove by use of a 5' end-labelled oligomer corresponding to the nucleotide of the 4th to 32nd from the 5'-end of the 5.85 rRNA gene (J.B.C. 252, 8118-8125 (1977)). And the EcoRI fragment of about 3 kb containing a part of each of 5.85rRNA gene and 25SrRNA gene was obtained by cleavage with EcoRI of the pRRN, which was then introduced at the EcoRI site derived from pBR322 of pILG2 to construct a plasmid pIRL9.

(ii-2) Construction of pALT18

ADH1 promoter+α-ALDCase gene+HIP1 terminator fragment was obtained according to the method shown below.

After cleavage of the the aforementioned plasmid pUAR5 having α-ALDCase gene with HincII, the fragment was treated with Bal31 and ligated to HindIII linker, and thereafter cleaved with HindIII and BamHI. The α-ALDCase gene fragment obtained was inserted between the BamHI and the HindIII sites of pUC12 (produced by Pharmacia Co.). The nucleotide sequences of these plasmids were determined, and to obtain a plasmid having about 40 bp upstream of 5'-end and the initial ATG of α-ALDCase gene deleted was selected, which plasmid was named pALDC3. The pALDC3 was digested with BamHI and made to have a blunt end with klenow fragment and then the HindIII-SmaI fragment of the aforementioned pAK503 was substituted with the α-ALDC gene fragment obtained by HindIII digestion to construct a plasmid pAL503-3. Further, the SphI site of the pAL503-3 was digested with SphI and then converted to the BamHI site by S1 nuclease treatment and BamHI linker addition, and thereafter ADHI promoter+α-ALDCase gene fragment was obtained as BamHI-BglII-O fragment.

On the other hand, a plasmid pHIPT was constructed, which was a modification of pBR322 in that the BamHI-SalI fragment of pBR322 was substituted with the BamHI-SalI fragment having about 0.9 kbp of the 3'-end non-translation region and about 0.1 kb of the 3' translation region of the HIP1 gene, which was constructed by cleavage with BamHI and SalI of the aforementioned plasmid pHIP1 having HIP1 gene above ADHI promoter+α-ALDCase gene fragment was inserted at the BamHI cite of this plasmid to construct a plasmid pALT18 in which ADH1 promoter+α-ALDCase gene+HIP1 terminator are linked in this order mentioned.

(ii-3) Construction of pIARL1

The ADH1 promoter+α-ALDCase gene+HIP1 terminator fragment obtained as the BamHI fragment after digestion of pALT18 with SalI and subsequent treatment with klenow fragment, addition of BamHI linker and BamHI digestion was inserted at the BglII site of pIRL9 to construct the desired plasmid pIARL2.

(5) Introduction of pIARL1 into Yeast and Expression of α-ALDCase Gene

By use of the pIARL1 constructed as described above, yeast was transformed as follows. Beer yeast IFO0751 was cultured in YPD medium at 30° C. to $OD_{600}=1.0$, and the cells were collected and transformed with pIARL1 according to the lithium acetate method. For promoting recombination in the rRNA gene sequence, pIARL1 was completely digested at the KpnI site within the rRNA gene sequence to be made linear before transformation. After transformation, $10^8$ of the yeast cells were suspended in 1 ml of YPD medium and shaked at 30° C. for 18 hours, and the culture was then spreaded onto YPD agar medium containing an antibiotic G418 (500 μg/m). Subsequently, the plate was incubated at 30° C. for 3 to 5 days to obtain colonies. In these colonies, in addition to the transformed cells, cells having acquired G418 resistance independently on pIARL1 were contained, and therefore they were transferred with a toothpick onto the agar medium containing X-gal (5'-bromo-4'-chloro-3'-indoyl-β-D galactoside) of Ruby et al (Method in Enzymology, vol. 101, p. 253 (1983)) and incubated at 30° C. for 2 to 5 days. Those which formed blue colony on this plate by β-galactosidase activity (Lac+ strain) were judged to be transformants. Such cells all exhibited α-ALDCase activity of 0.8–1.8 U/mg protein. The transformant exhibiting the highest α-ALDCase activity (SKB103) was cultured in YPD medium non-selectively for 80 generations. The α-ALDCase activity after cultivation was found to be 0.9 U/mg protein, indicating that the gene exhibiting α-ALDCase activity was stably held in the chromosome.

(6) Excision of Undesired Sequence and Expression of α-ALDCase gene

After non-selective cultivation of the transformant obtained in (5) (SKB103) in YPD medium for 20 to 30 generations, the culture was adequately diluted and spreaded onto the agar medium containing X-gal of Ruby et al as described above. The plate was cultured at 30° C. for 5 to 7 days, and the strains without blue color colony formation (Lac− strain) were selected. Of these strains, those exhibiting G418 sensitivity on YPD agar medium containing 500 μg/ml G418 were selected. Further, strains exhibiting α-ALDCase activity were obtained. In these strains, as shown in it may be considered that, recombination occurred between the duplicated rRNA gene sequences, whereby only ADH1 promoter, α-ALDCase gene and HIP1 terminator remain on the chromosome, with other vector portions being excised.

Of these strains, the strain exhibiting α-ALDCase activity of 0.2 U/mg protein (SKB104) was cultured in YPD medium for 40 generations and activity of 80% or more was maintained.

(7) Fermentation Test

Fermentation tests were conducted for the SKB103 obtained in (5) and the SKB104 obtained in (6), and reduction of TDA in fermented wort was confirmed according to the following method. Two kinds of yeasts were subjected to stationary cultivation non selectively in YPD medium at 20° C. for 3 days and subsequently at 10° C. for 10 days, and the respective cells were collected by centrifugation at 3000×g for 10 minutes, washed with distilled water and then provided for fermentation test.

To a wort adjusted to 11° P was added the yeast to a yeast addition ratio of 0.6% (wet. w/v) and, after sufficient aeration, stationary Fermentation was carried out at 10° C. for 8 to 10 days. After completion of fermentation, cells were removed by centrifugation at 3000×g for 10 minutes and filtration, and the filtrate was subjected to measurement of amount of TDA and apparent extract. The results were as shown in the following Tables. Although both cultivation and fermentation were conducted under non-selective conditions, marked decrease in amount of TDA in fermented wort was seen as compared with control strain, thus indicating that α-ALDCase activity was stably exhibited.

Results of Fermentation Test of SKB103

| Strain | TDA (mg/liter) | Apparent extract (°P.) |
| --- | --- | --- |
| IFO 0751 ① | 0.68 | 2.4 |
| ② | 0.69 | 2.2 |
| Average | 0.69 | 2.3 |
| SKB 103 ① | 0.14 | 2.7 |
| ② | 0.14 | 2.9 |
| Average | 0.14 | 2.8 |

Results of Fermentation Test of SKB104

| Strain | TDA (mg/liter) | Apparent extract (°P.) |
| --- | --- | --- |
| IFO 0751 ① | 1.02 | 2.3 |
| ② | 0.94 | 2.2 |
| Average | 0.98 | 2.3 |
| SKB 104 ① | 0.44 | 2.2 |
| ② | 0.51 | 2.0 |
| Average | 0.48 | 2.1 |

Deposition of Microorganism

The microorganisms shown below related to the present invention have been deposited at the Institute of Fermentation Research, Agency of Industrial Science & Technology, Ministry of International Trade and Industry under the following deposition numbers under the Budapest Treaty on the International Recognition of the Deposit of Microorganisms for the Purposes of Patent Procedure.

(1) SKB101 (containing pALG5034) ... FERM-BP No. 1228
(2) SKB102 (containing pALG5034) ... FERM-BP No. 1229
  Both of (1) and (2) were deposited on December 11, 1985.
(3) SKB104 ... FERM-BP No. 1227
  (3) was deposited on December 2, 1986.

What is claimed is:

1. An isolated DNA sequence which has a nucleotide sequence coding for a polypeptide having α-acetolactate decarboxylase activity, of which amino acid sequence is substantially from A to B of the amino acid sequence shown in FIG. 1.

2. An isolated DNA sequence of claim 1, which has a nucleotide sequence of from A to B of the nucleotide sequence shown in FIG. 1 or its degenerative isomer.

3. A yeast belonging to Saccharomyces cerevisiae, having reduced α-acetolactate producing ability which has been transformed with a DNA sequence which has a nucleotide sequence coding for a polypeptide having α-acetolactate decarboxylase activity, of which amino acid sequence is substantially from A to B of the amino acid sequence shown in FIG. 1.

4. A yeast according to claim 3, wherein the nucleotide sequence is contained in a plasmid.

5. A yeast according to claim 3, wherein the DNA sequence has the nucleotide sequence of from A to B of the nucleotide sequence shown in FIG. 1.

6. A process for producing a yeast having reduced α-acetolactate producing ability, which process comprises transforming a host yeast belonging to Saccharomyces cerevisiae with a DNA sequence which has a nucleotide sequence coding for a polypeptide having α-acetolactate decarboxylase activity, of which amino acid sequence is substantially from A to B of the amino acid sequence shown in FIG. 1.

7. A process for producing a yeast having reduced α-acetolactate producing ability as claimed in claim 6, wherein the nucleotide sequence is one from A to B of the nucleotide sequence shown in FIG. 1 or its degenerative isomer.

8. A process for producing a yeast having reduced α-acetolactate producing ability as claimed in claim 6, wherein the nucleotide sequence is contained in a plasmid.

9. A process for producing a yeast having reduced α-acetolactate producing ability as claimed in claim 7, wherein the DNA sequence has the nucleotide sequence of from A to B of the nucleotide sequence shown in FIG. 1.

10. A process for producing an alcoholic beverage wherein a yeast is caused to act upon its substrate to produce ethanol therefrom, the improvement which comprises the use of a yeast belonging to Saccharomyces cerevisiae having reduced α-acetolactate producing ability, which yeast has been transformed with a DNA sequence which has a nucleotide sequence coding for a polypeptide having α-acetolactate decarboxylase activity, of which amino acid sequence is substantially from A to B of the amino acid sequence shown in FIG. 1.

11. The process for producing an alcoholic beverage as claimed in claim 10, wherein the nucleotide sequence is contained in a plasmid.

12. The process for producing an alcoholic beverage as claimed in claim 10, wherein the DNA sequence has a nucleotide sequence of from A to B of the nucleotide sequence shown in FIG. 1.

13. The process for producing an alcoholic beverage as claimed in claim 10, wherein the alcoholic beverage is beer.

14. A recombinant DNA vector having a DNA sequence which has a nucleotide sequence coding for a polypeptide having α-acetolactate decarboxylase activity, of which the amino acid sequence is substantially from A to B of the amino acid sequence shown in FIG. 1.

* * * * *

UNITED STATES PATENT AND TRADEMARK OFFICE
CERTIFICATE OF CORRECTION

PATENT NO. : 4,895,802

DATED : January 23, 1990

INVENTOR(S) : Hidetaka SONE ET AL

It is certified that error appears in the above-identified patent and that said Letters Patent is hereby corrected as shown below:

Title page, item [30]:

after "Dec. 13, 1985 [JP] Japan ................ 60-280289"
insert --Dec. 4, 1986 [JP] Japan ............... 61-289571--

Signed and Sealed this

Thirtieth Day of July, 1991

Attest:

HARRY F. MANBECK, JR.

*Attesting Officer*  *Commissioner of Patents and Trademarks*